(12) United States Patent
Jha et al.

(10) Patent No.: US 11,540,980 B2
(45) Date of Patent: Jan. 3, 2023

(54) PERSONAL CARE COMPOSITIONS AND METHODS FOR THE SAME

(71) Applicant: COLGATE-PALMOLIVE COMPANY, New York, NY (US)

(72) Inventors: Brajesh Jha, Midlothian, VA (US); Katie Truong, Piscataway, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/722,725

(22) Filed: Dec. 20, 2019

(65) Prior Publication Data

US 2021/0186827 A1 Jun. 24, 2021

(51) Int. Cl.
*A61K 8/04* (2006.01)
*A61K 8/73* (2006.01)
*A61Q 5/02* (2006.01)
*A61Q 19/10* (2006.01)
*A61Q 11/00* (2006.01)

(52) U.S. Cl.
CPC .............. *A61K 8/046* (2013.01); *A61K 8/73* (2013.01); *A61Q 5/02* (2013.01); *A61Q 11/00* (2013.01); *A61Q 19/10* (2013.01)

(58) Field of Classification Search
CPC . A61K 8/046; A61K 8/73; A61Q 5/02; A61Q 11/02; A61Q 19/10
See application file for complete search history.

(56) References Cited

U.S. PATENT DOCUMENTS

| | | | |
|---|---|---|---|
| 4,571,338 A * | 2/1986 | Okonogi | A23L 29/27 426/324 |
| 5,607,678 A | 3/1997 | Moore et al. | |
| 6,265,368 B1 | 7/2001 | Aronson et al. | |
| 2005/0118130 A1 | 6/2005 | Utz et al. | |
| 2007/0166243 A1* | 7/2007 | Yoshida | A61Q 11/00 424/49 |
| 2008/0287300 A1 | 11/2008 | Kopesky et al. | |
| 2011/0243861 A1* | 10/2011 | Vierling | A61K 8/604 424/49 |
| 2012/0183484 A1* | 7/2012 | Beaumer | A61K 8/73 424/70.13 |
| 2013/0287708 A1* | 10/2013 | Silberstein | A61K 8/553 424/49 |
| 2016/0022552 A1* | 1/2016 | Kim | C11D 3/2041 510/158 |
| 2016/0199292 A1 | 7/2016 | Farnum | |
| 2017/0095410 A1 | 4/2017 | Hara et al. | |

FOREIGN PATENT DOCUMENTS

| | | |
|---|---|---|
| EP | 2371348 | 10/2011 |
| WO | 1999/051716 | 10/1999 |
| WO | 2010/143196 | 12/2010 |
| WO | 2017/209088 | 12/2017 |

OTHER PUBLICATIONS

Google_search_Aug. 14, 2021_carrageenan_and_xanthan_gum_synergy (Year: 2021).*
International Search Report and the Written Opinion of the International Searching Authority issued in International Application PCT/US2020/070857 dated Mar. 4, 2021.
Procter & Gamble, 2020, "Sensitivity and Gum Balm Medicinal Toothpaste", Mintel Database GNPD AN: 8155453.
Vichy, 2020, "Volcanic Mattifying Cleansing Cream", Mintel Database GNPD AN: 8056441.

* cited by examiner

Primary Examiner — Michael P Cohen

(57) ABSTRACT

A personal care composition and methods for generating increased foam volume in the personal care composition are disclosed. The personal care composition may include a carrier and at least two hydrocolloids, wherein the at least two hydrocolloids are present in an effective amount to produce increased foam volume. The method may include contacting a carrier of the personal care composition with at least two hydrocolloids. The at least two hydrocolloids may include xanthan gum and carrageenan in a ratio of from about 1.5:1 to about 9:1.

11 Claims, 1 Drawing Sheet

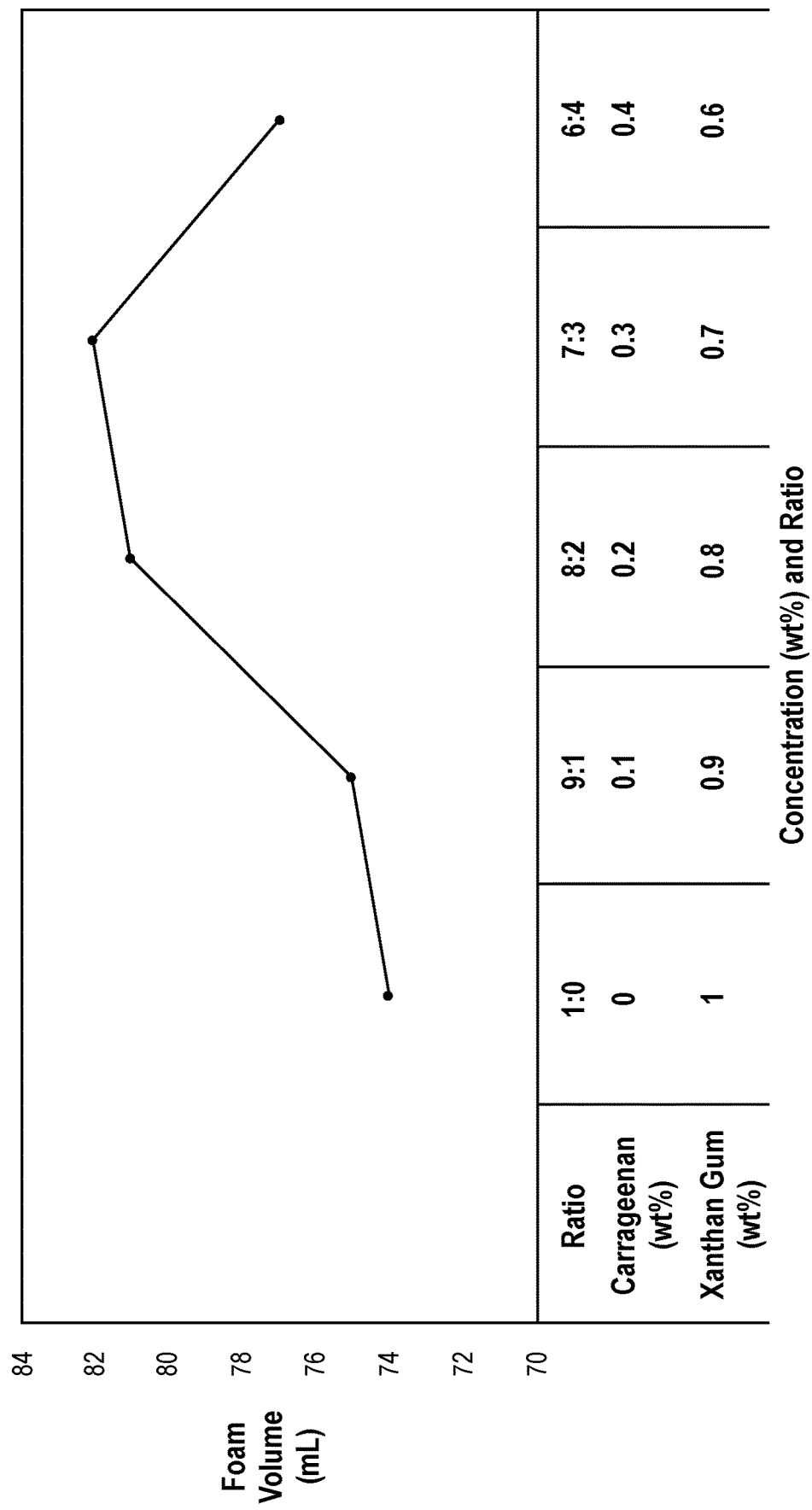

PERSONAL CARE COMPOSITIONS AND METHODS FOR THE SAME

BACKGROUND

Foaming and/or lather are crucial properties related to consumer acceptance of personal care compositions, such as body washes and toothpastes. For example, improved foaming and lather is often perceived by consumers as being directly related to improved cleaning. While conventional personal care compositions generally exhibit acceptable foaming and lather, the search for compositions and additives having improved foaming and lather is ongoing.

What is needed, then, are compositions exhibiting improved foaming and/or lather and methods for the same.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a personal care composition including a carrier and at least two hydrocolloids, wherein the at least two hydrocolloids are present in an effective amount to produce increased foam volume.

In at least one example, a first hydrocolloid of the at least two hydrocolloids may include a sulfated polysaccharide. In at least one example, the sulfated polysaccharide may include one or more of carrageenan, keratan sulfate, chondroitin sulfate, dextran sulfate, dermatan sulfate, fucoidan, funoran, heparin, porphyran, or combinations thereof. In another example, the sulfated polysaccharide may also be selected from the group consisting of carrageenan, keratan sulfate, chondroitin sulfate, dextran sulfate, dermatan sulfate, fucoidan, funoran, heparin, porphyran, and combinations thereof. In yet another example, the sulfated polysaccharide is carrageenan. The carrageenan may include one or more of kappa-carrageenan, iota-carrageenan, lambda-carrageenan, or a combination thereof.

In at least one example, the at least two hydrocolloids may include xanthan gum.

In at least one example, a first hydrocolloid of the at least two hydrocolloids may include a sulfated polysaccharide, and a second hydrocolloid of the at least two hydrocolloids may include xanthan gum. In at least one example, the sulfated polysaccharide may include one or more of carrageenan, keratan sulfate, chondroitin sulfate, dextran sulfate, dermatan sulfate, fucoidan, funoran, heparin, porphyran, or combinations thereof. In another example, the sulfated polysaccharide may also be selected from the group consisting of carrageenan, keratan sulfate, chondroitin sulfate, dextran sulfate, dermatan sulfate, fucoidan, funoran, heparin, porphyran, and combinations thereof. In yet another example, the sulfated polysaccharide is carrageenan. The carrageenan may include one or more of kappa-carrageenan, iota-carrageenan, lambda-carrageenan, or a combination thereof.

In at least one example, the xanthan gum and the sulfated polysaccharide may be present in the personal care composition in a ratio of from about 1.5:1 to about 9:1.

In at least one example, the xanthan gum and the sulfated polysaccharide may be present in the personal care composition in a ratio of from about 2.3:1 to about 9:1.

In at least one example, the xanthan gum and the sulfated polysaccharide may be present in the personal care composition in a ratio of from about 2.3:1 to about 4:1.

In at least one example, a first hydrocolloid of the at least two hydrocolloids may include a sulfated polysaccharide, wherein the polysaccharide is carrageenan, and wherein a second hydrocolloid of the at least two hydrocolloids may include xanthan gum. In at least one example, the xanthan gum and the carrageenan may be present in the personal care composition in a ratio of from about 1.5:1 to about 9:1. In another example, the xanthan gum and the carrageenan may be present in the personal care composition in a ratio of from about 2.3:1 to about 9:1. In yet another example, the xanthan gum and the carrageenan may be present in the personal care composition in a ratio of from about 2.3:1 to about 4:1.

In at least one example, the personal care composition is selected from the group consisting of a shampoo, a shower gel, a body wash, a liquid soap, and a face wash.

In at least one example, the personal care composition is an oral care composition and the carrier is an orally acceptable vehicle. In at least one example, the oral care composition is selected from the group consisting of a toothpaste and a tooth gel.

The foregoing and/or other aspects and utilities embodied in the present disclosure may be achieved by providing a method for preparing any one or more of the personal care compositions disclosed herein. The method may include contacting a carrier and at least two hydrocolloids with one another.

The foregoing and/or other aspects and utilities embodied in the present disclosure may be achieved by providing a method for generating increased foam volume in a personal care composition. The method may include contacting a carrier of the personal care composition with at least two hydrocolloids, wherein the at least two hydrocolloids include xanthan gum and carrageenan in a ratio of from about 1.5:1 to about 9:1.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

BRIEF DESCRIPTION OF THE DRAWINGS

The accompanying drawings, which are incorporated in and constitute a part of this specification, illustrate embodiments of the present teachings. These and/or other aspects and advantages in the embodiments of the disclosure will become apparent and more readily appreciated from the following description of the various embodiments, taken in conjunction with the accompanying drawings of which:

FIG. 1 is a plot of foam volume with respect to amounts and ratios of xanthan gum and carrageenan in the personal care compositions (1)-(5) of Example 1, according to one or more embodiments disclosed.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

As used herein, "free" or "substantially free" of a material may refer to a composition, component, or phase where the material is present in an amount of less than 10.0 weight %, less than 5.0 weight %, less than 3.0 weight %, less than 1.0 weight %, less than 0.1 weight %, less than 0.05 weight %, less than 0.01 weight %, less than 0.005 weight %, or less than 0.0001 weight % based on a total weight of the composition, component, or phase.

All references cited herein are hereby incorporated by reference in their entireties. In the event of a conflict in a definition in the present disclosure and that of a cited reference, the present disclosure controls.

The present inventors have surprisingly and unexpectedly discovered that personal care compositions including a synergistic combination of at least two hydrocolloids at a ratio of from about 6:4 (or 1.5:1) to about 9:1 exhibit synergistic results with respect to the generation of foam. Particularly, the present inventors have surprisingly and unexpectedly discovered that personal care compositions including a synergistic combination of xanthan gum and carrageenan at a ratio of from about 6:4 (or 1.5:1) to about 9:1 exhibit synergistic results with respect to the generation of foam. The surprising and unexpected increase in foam generation is especially exhibited or more pronounced when xanthan gum and carrageenan are provided in a ratio of from about 7:3 (or 2.3:1) to about 9:1.

Compositions

Compositions disclosed herein may be or include a personal care composition. For example, the compositions disclosed herein may be or include a personal care composition or a personal care product for cleaning. As used herein, the term or expression "personal care composition" may refer to a composition for application to skin, hair, an oral cavity (e.g., mouth) or a surface thereof, of a mammal, especially a human. It should be appreciated that personal care compositions, as used herein, may also include oral care compositions and oral care products. As used herein, the term or expression "oral care product" or "oral care composition" may refer to a product or composition, respectively, for cleaning an oral cavity or surface thereof. The personal care composition may be a leave-on personal care composition, a rinse off personal care composition, or the like. The personal care composition may include any product or composition for cleaning a human body or portion thereof. The personal care composition may be in any suitable form. Illustrative forms of the personal care composition may be or include, but is not limited to, a liquid, a cream, a foam, a scrub, a gel (e.g., shower gel, tooth gel), a solid (e.g., solid bar soap), a paste (e.g., toothpaste), or the like. Illustrative personal care compositions may be or include, but are not limited to, cleansers, emulsions, shampoos, conditioners, shower gels, body washes, soaps, including bar soaps and liquid soaps (e.g., liquid hand soaps), face washes, a toothpaste (dentifrice), a prophylactic paste, a tooth powder, a tooth polish, a tooth gel (e.g., a whitening gel), a gel or paste coated on an application support such as dental floss or a toothbrush (e.g., a manual, electric, sound, a combination thereof or ultrasound toothbrush), or the like.

In an exemplary implementation, the personal care compositions disclosed herein may include a carrier and a plurality of hydrocolloids or a combination of at least two hydrocolloids. The personal care compositions may include the carrier and a combination of least two hydrocolloids, where the hydrocolloids are present in a synergistic amount and/or ratio. For example, as further described herein, the combination, amount, and/or ratio of the at least two hydrocolloids interact synergistically with one another to generate increased foam or foam volume in the personal care composition as compared to personal care compositions without the synergistic combination, amount, and/or ratio. In at least one implementation, the personal care composition includes a synergistic combination, amount, and/or ratio of xanthan gum and carrageenan.

As used herein, the term "hydrocolloid" may refer to a heterogenous group of long chain polymers, such as polysaccharides and proteins, characterized by their property of forming viscous dispersions and/or gels when contacted with water. Hydrocolloids are generally functionalized with a large number of hydroxyl (—OH) groups, which increases their affinity for binding water and renders them hydrophilic compounds. Illustrative hydrocolloids of the personal care compositions disclosed herein may be or include, but are not limited to, xanthan gum, guar gum, locust bean gum, gelatin, carrageenan, polygeenan, alginate, pectin, psyllium husk fiber, agar, beta glucan, gellan gum, konjac, carob bean gum, gum Arabic, ghatti gum, tara gum, tragacanth gum, gellan, methyl cellulose, hydroxypropylmethyl cellulose, chitosan, chitin, propylene glycol alginate, or the like, or mixtures and combinations thereof. In an exemplary implementation, the composition includes a combination of at least xanthan gum and carrageenan. For example, the hydrocolloids of the personal care compositions disclosed herein may comprise, consist of, or consist essentially of xanthan gum and carrageenan.

In at least one implementation, the hydrocolloids include at least one sulfated polysaccharide or a salt thereof. The sulfated polysaccharide may be a linear sulfated polysaccharide having one or more sulphate groups. The sulfated polysaccharides may be derived, extracted, or otherwise obtained from a natural source, such as from red algae *Furcellaria lumbricalisc*. The sulfated polysaccharides may also be synthesized by reacting neutral polysaccharides or natural sulfated polysaccharides with a sulfating reagent. Illustrative sulfated polysaccharides may include, but are not limited to, carrageenan, keratan sulfate, chondroitin sulfate, dextran sulfate, dermatan sulfate, fucoidan, funoran, heparin, porphyran, or the like, or combinations thereof. The sulfated polysaccharides may also include salts of the sulfated polysaccharides, such alkali metal salts or alkaline earth metal salts of the sulfated polysaccharides. Illustrative sulfated polysaccharides may also include those derived from or contained in DANAGEL™, GELCARIN®, ISAGEL™, LACTARIN®, LACTOGEL™, SEAGEL®, SEAKEM®, SEASPEN®, VISCARIN®, or the like, or any combination thereof, each of which include carrageenan (CAS #9000-07-1) and are commercially available from FMC BioPolymer Corp. of Philadelphia, Pa. In at least one implementation, the hydrocolloids include the sulfated polysaccharide, carrageenan. The carrageenan may include one or more of the following: kappa-carrageenan (one sulfate group per disaccharide), iota-carrageenan (two sulfate groups per disaccharide), lambda-carrageenan (three sulfate groups per disaccharide), or any mixture or combination thereof. In a preferred implementation, the sulfated polysaccharide includes at least kappa-carrageenan.

The hydrocolloids may be present in the personal care composition in an effect amount. As used herein, the expression "effective amount of the hydrocolloids" or the like may refer to an amount of each of the hydrocolloids sufficient to work or interact synergistically with one another to elicit a response, such as increased generation of foam. For example, a first hydrocolloid, such as xanthan gum, may be present in the personal care composition in an effective amount to interact or work synergistically with a second hydrocolloid, such as carrageenan, to produce increased foam volume.

The amount or concentration of any one or more of the hydrocolloids present in the personal care composition may vary widely. In at least one implementation, the amount of any one or more of the hydrocolloids (e.g., each or a combination) present in the personal care composition may be from greater than 0 weight % to less than or equal to about 40 weight %, based on a total weight of the personal care composition. For example any one or more of the hydrocolloids may be present in the personal care composition in an amount of from greater than 0 weight %, about 0.00025 weight %, about 0.0001 weight %, about 0.001 weight %, about 0.01 weight %, about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1 weight %, about 1.2 weight %, about 1.4 weight %, about 1.6 weight %, about 1.8 weight %, about 2 weight %, about 3 weight %, about 4 weight %, about 5 weight %, about 6 weight %, about 7 weight %, about 8 weight %, about 9 weight %, about 10 weight %, about 15 weight %, or about 20 weight % to about 25 weight %, about 30 weight %, about 35 weight %, about 40 weight %, based on a total weight of the personal care composition. In another example, any one or more of the hydrocolloids may be present in the personal care composition in an amount of at least 0.00001 wt %, at least 0.0001 weight %, at least 0.001 weight %, at least 0.01 weight %, at least 0.1 weight %, at least 0.2 weight %, at least 0.3 weight %, at least 0.4 weight %, at least 0.5 weight %, at least 0.6 weight %, at least 0.7 weight %, at least 0.8 weight %, at least 0.9 weight %, at least 1.0 weight %, at least 1.5 weight %, at least 2.0 weight %, at least 2.5 weight %, at least 3.0 weight %, at least 3.5 weight %, at least 4.0 weight %, at least 5 weight %, at least 10 weight %, at least 20 at least %, at least 30 weight %, or more, based on a total weight of the personal care composition. In yet another example, any one or more of the hydrocolloids may be present in the personal care composition in an amount of from greater than 0 weight % to less than 40 weight %, less than 35 weight %, less than 30 weight %, less than 25 weight %, less than 20 weight %, less than 15 weight %, less than 10 weight %, less than 9 weight %, less than 8 weight %, less than 7 weight %, less than 6 weight %, less than 5 weight %, less than 4 weight %, less than 3 weight %, less than 2 weight %, less than 1 weight %, less than 0.9 weight %, less than 0.8 weight %, less than 0.7 weight %, less than 0.6 weight %, less than 0.5 weight %, less than 0.4 weight %, less than 0.3 weight %, less than 0.2 weight %, less than 0.1 weight %, less than 0.01 weight %, less than 0.001 weight %, less than 0.0001 weight %, less than 0.00001 weight %, based on a total weight of the personal care composition.

In an exemplary implementation, the total amount of the hydrocolloids present in the personal care composition may be from greater than 0 weight % to about 50 weight %. For example, the total amount of the hydrocolloids present in the personal care composition may be from about 0.5 weight % to about 1.5 weight %, more preferably about 0.8 weight % to about 1.2 weight %, even more preferably about 1 weight %, based on a total weight of the personal care composition. In at least one implementation, the hydrocolloids include a combination of xanthan gum and carrageenan, where the xanthan gum is present in an amount of from about 0.5 weight % to about 0.9 weight % or about 0.6 weight % to about 0.9 weight %, and where the carrageenan is present in an amount of from about 0.1 weight % to about 0.4 weight % or about 0.2 weight % to about 0.3 weight %, based on a total weight of the personal care composition.

The hydrocolloids may be present in an effective ratio (i.e., concentration, weight, or volume ratio) to elicit a response. For example, a first hydrocolloid and a second hydrocolloid may be present in an effective ratio to interact or work synergistically with one another to produce increased foam volume. In a preferred implementation, xanthan gum and carrageenan are present in an effective ratio to interact or work synergistically with one another to produce increased foam volume.

In at least one implementation, the concentration or weight ratio of a first hydrocolloid to a second hydrocolloid may be from about 0.5:1 to about 15:1. For example, the ratio of the first hydrocolloid to the second hydrocolloid may be from about 0.5:1, about 0.6:1, about 0.7:1, about 0.8:1, about 0.9:1, about 1:1, about 1.1:1, about 1.2:1, about 1.3:1, about 1.4:1, about 1.5:1, about 1.6:1, about 1.7:1, about 1.8:1, about 1.9:1, about 2:1, about 2.1:1, about 2.2:1, about 2.3:1, about 2.4:1, about 2.5:1, about 2.6:1, about 2.7:1, about 2.8:1, about 2.9:1, or about 3:1 to about 3.1:1, about 3.2:1, about 3.3:1, about 3.4:1, about 3.5:1, about 3.6:1, about 3.7:1, about 3.8:1, about 3.9:1, about 4:1, about 4.2:1, about 4.4:1, about 4.6:1, about 4.8:1, about 5:1, about 5.2:1, about 5.4:1, about 5.6:1, about 5.8:1, about 6:1, about 6.2:1, about 6.4:1, about 6.6:1, about 6.8:1, about 7:1, about 7.2:1, about 7.4:1, about 7.6:1, about 7.8:1, about 8:1, about 8.2:1, about 8.4:1, about 8.6:1, about 8.8:1, about 9:1, about 10:1, about 11:1, about 12:1, about 13:1, about 14:1, or about 15:1. In another example, the ratio of the first hydrocolloid to the second hydrocolloid may be greater than or equal to about 0.5:1, greater than or equal to about 0.6:1, greater than or equal to about 0.7:1, greater than or equal to about 0.8:1, greater than or equal to about 0.9:1, greater than or equal to about 1:1, greater than or equal to about 1.1:1, greater than or equal to about 1.2:1, greater than or equal to about 1.3:1, greater than or equal to about 1.4:1, greater than or equal to about 1.5:1, greater than or equal to about 1.6:1, greater than or equal to about 1.7:1, greater than or equal to about 1.8:1, greater than or equal to about 1.9:1, greater than or equal to about 2:1, greater than or equal to about 2.1:1, greater than or equal to about 2.2:1, greater than or equal to about 2.3:1, greater than or equal to about 2.4:1, or greater than or equal to about 2.5:1, or greater. In another example, the ratio of the first hydrocolloid to the second hydrocolloid may be less than or equal to 15:1, less than or equal to 14:1, less than or equal to 13:1, less than or equal to 12:1, less than or equal to 11:1, less than or equal to 10:1, less than or equal to 9:1, less than or equal to 8.8:1, less than or equal to 8.6:1, less than or equal to 8.4:1, less than or equal to 8.2:1, less than or equal to 8:1, less than or equal to 7.8:1, less than or equal to 7.6:1, less than or equal to 7.4:1, less than or equal to 7.2:1, less than or equal to 7:1, less than or equal to 6.8:1, less than or equal to 6.6:1, less than or equal to 6.4:1, less than or equal to 6.2:1, less than or equal to 6:1, less than or equal to 5.8:1, less than or equal to 5.6:1, less than or equal to 5.4:1, less than or equal to 5.2:1, less than or equal to 5:1, less than or equal to 4.8:1, less than or equal to 4.6:1, less than or equal to 4.4:1, less than or equal to 4.2:1, less than or equal to 4:1, or less. In an exemplary implementation, the first hydrocolloid may be xanthan gum and the second hydrocolloid may be carrageenan, and the ratio of the xanthan gum to the carrageenan may be from about 1.5:1 to about 9:1, more preferably about 2.3:1 to about 9:1, or from about 2.3:1 to about 4:1.

As discussed above, the personal care composition may include the carrier and a combination of at least two hydrocolloids. The personal care composition may include the hydrocolloids mixed with, dissolved in, combined with, or otherwise contacted with the carrier and/or one or more excipients. In at least one implementation, the carrier may be capable of or configured to store, entrain, or otherwise contain the hydrocolloids. It should be appreciated that the components or contents of the carrier and the respective amount of each of the components of the carrier may be at least partially determined by the type or use of the personal care product or the personal care composition thereof.

In at least one implementation, the personal care product or the personal care composition thereof may be or include a cleanser, an emulsion, a shampoo, a shower gel, a body wash, a soap, including bar soaps and liquid soaps (e.g., liquid hand soaps), a face wash, or the like. In a preferred implementation, the personal care product or the composition thereof that includes the hydrocolloids and the carrier is a liquid personal care product or a liquid personal care composition, such as a shower gel or a body wash.

In at least one implementation, the personal care product or the composition thereof may be a personal hand and/or body cleansing composition. Illustrative personal hand and/or body cleansing compositions may include, but are not limited to, liquid soaps, bar soaps, body washes, shower gels, or the like. In a preferred implementation, the personal hand and/or body cleansing composition is a liquid personal hand and/or liquid body cleansing composition, such as a shower gel or a body wash. The carrier for the personal hand and/or body cleansing composition may include, but is not limited to, any one or more of the following: fragrances, essential oils, emulsifying agents, thickening agents, colorants, surfactants, natural actives, therapeutic actives, stain prevention actives, antimicrobial agents, vitamins, natural extracts, amino acids, enzymes and/or other proteins, abrasives, odor control agents, conditioning agents, moisturizers, humectants, occlusive agents, skin lipid fluidizers, lipophilic actives, hydrophilic materials, pearlizers, opacifying agents, sodium soaps, titanium dioxide, fragrances, or the like, or any mixture or combination thereof, in addition to any one or more of the carrier components disclosed herein.

In at least one implementation, the carrier is an orally acceptable vehicle. For example, the personal care composition may be an oral care product or an oral care composition thereof including the hydrocolloids and the carrier (i.e., the orally acceptable vehicle). In at least one implementation, the hydrocolloids may be dispersed and/or disposed in the orally acceptable vehicle. As used herein, the expression "orally acceptable vehicle" may refer to a suitable vehicle, ingredient, or combination of ingredients, which may be used to suspend, hold, mobilize, or otherwise contain the hydrocolloids in a safe and effective manner. For example, the orally acceptable vehicle may be or include a suitable solvent, solution, or medium, and the hydrocolloids may be dispersed, dissolved, mixed, or otherwise contacted with the suitable solvent, solution, or medium to prepare or form the oral care product or the oral care composition thereof. The orally acceptable vehicle may include any known ingredients or additives of conventional oral care compositions. The orally acceptable vehicle may include various dentifrice ingredients to adjust the rheology and feel of the oral care composition.

In at least one implementation, the orally acceptable vehicle may include one or more humectants. Illustrative humectants may be or include, but are not limited to, glycerin, propylene glycol, polyethylene glycol, sorbitol, xylitol, or the like, or any mixture or combination thereof. In a preferred implementation, the orally acceptable vehicle may be or include, but is not limited to, sorbitol. The one or more humectants may be present in the oral care composition in an amount of from about 5 weight % to about 35 weight %, based on a total weight of the personal care composition.

In at least one implementation, the orally acceptable vehicle may include an orally acceptable solvent. Illustrative solvents may include, but are not limited to, one or more of ethanol, phenoxyethanol, isopropanol, water, cyclohexane, methyl glycol acetate, benzyl alcohol, or the like, or any mixture or combination thereof. In a preferred implementation, the orally acceptable solvent includes benzyl alcohol.

It should be appreciated that the orally acceptable vehicle may also include materials such as, but not limited to, one or more antibacterial agents, fluoride ion sources, anticalculus agents, buffers, flavoring agents, sources of peroxide (e.g., hydrogen peroxide), alkali metal bicarbonate salts, thickening materials, antimicrobial agents, humectants, additional water, surfactants, titanium dioxide, cooling agents, coloring agents, or the like, or mixtures or combinations thereof.

The carrier may be hydrophilic or hydrophobic. The carrier may be anhydrous. The carrier may be a liquid or a solid at room temperature. The carrier may have a viscosity of from about 2,000 centipoise (cP) to about 200,000 cP. For example, the carrier for a shower gel or a body wash may have a viscosity of from about 2,000 cP to about 16,000 cP. In another example, the carrier for an oral care composition, such as a toothpaste, may have a viscosity of from about 50,000 cP to about 150,000 cP. Accordingly, it should be appreciated that the viscosity of the carrier may vary and may at least partially depend on the type of personal care composition in which the synergistic combination of the hydrocolloids is utilized. In an exemplary implementation, the carrier is a liquid at room temperature.

As discussed above, the carrier of the personal care composition may include one or more surfactants. In at least one implementation, the one or more surfactants may be or include a salt of a $C_{10-16}$ alcohol ethoxylate sulfate, a betaine surfactant, an alkyl polyglucoside, or combinations thereof. In another implementation, the personal care composition may include one or more anionic surfactants, one or more cationic surfactants, one or more zwitterionic surfactants, one or more nonionic surfactants, or mixtures thereof. The amount of any one or more of the surfactants present in the personal care composition may be from about 1.0 wt % to about 50.0 wt %. For example, the amount of the surfactants in the personal care composition may be from about 1.0 wt %, about 5.0 wt %, about 10.0 wt %, about 15.0 wt % or about 20.0 wt % to about 25.0 wt %, about 30.0 wt %, about 35.0 wt %, about 40.0 wt %, or about 50.0 wt %, based on a total weight of the personal care composition.

The salt of the $C_{10-16}$ alcohol ethoxylate sulfate surfactant of the carrier may be any one or more salts of the $C_{10-16}$ alcohol ethoxylate sulfate. In at least one example, the $C_{10-16}$ may be lauryl. The average moles of ethylene oxide may be from 1 to 30. In a preferred implementation, the average moles of the ethylene oxide is 1 to 3. The cation of the salt may be any suitable cation of the $C_{10-16}$ alcohol ethoxylate sulfate. For example, the cation may be an alkali metal (e.g., sodium, potassium, etc.), an alkaline earth metal (e.g., calcium), ammonium, triethanolamine, or the like. In an exemplary implementation, the salt of the $C_{10-16}$ alcohol ethoxylate sulfate is sodium lauryl ether sulfate. The sodium lauryl ether sulfate may have an average of 2 moles of the ethylene oxide.

Illustrative betaine surfactants of the carrier may include, but are not limited to, cocodimethylcarboxymethyl betaine, cocamidopropyl betaine, lauryldimethylcarboxymethyl betaine, lauryldimethylcarboxyethyl betaine, cetyldimethylcarboxymethyl betaine, lauryl-bis-(2-hydroxyethyl)carboxymethyl betaine, oleyldimethylgammacarboxypropyl betaine, and lauryl-bis-(2-hydroxypropyl)-carboxyethyl betaine, or the like, or combinations thereof. In a preferred embodiment, the betaine surfactant is a cocamidopropyl betaine.

The alkyl polyglucoside surfactant of the carrier may be represented by Formula (1):

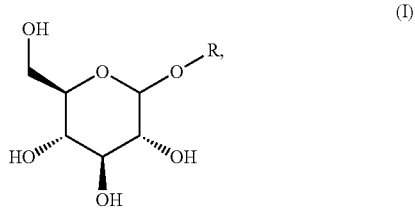

(I)

wherein R is a $C_{2-20}$ alkyl (such as a $C_{4-14}$ alkyl). Illustrative alkyl polyglucosides may be or include, but are not limited to, capryl glucoside, decyl glucoside, coco-glucoside, lauryl glucoside, or the like, or combinations thereof. In an exemplary implementation, the surfactants of the carrier include alkyl polyglucosides, preferably decyl glucoside, cocoglucoside, or combinations thereof.

In at least one embodiment, the personal care composition may include at least one anionic surfactant. Illustrative anionic surfactants may include, but are not limited to, water-soluble salts of higher fatty acid monoglyceride monosulfates, such as a sodium salt of a monosulfated monoglyceride of hydrogenated coconut oil fatty acids, such as sodium N-methyl N-cocoyl taurate, sodium cocomonoglyceride sulfate, or the like, or combinations thereof. Illustrative anionic surfactants may also include higher alkyl sulfates. As used herein, "higher alkyl" refers to $C_{6-30}$ alkyl. For example, the anionic surfactant may be or include sodium lauryl sulfate. The anionic surfactants may also include higher alkyl-ether sulfates. In another embodiment, the anionic surfactant may include higher alkyl aryl sulfonates, such as sodium dodecyl benzene sulfonate (sodium lauryl benzene sulfonate), and higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide), sodium lauryl sarcosinate, or the like, or combinations thereof. In an exemplary embodiment, the anionic surfactant may be or include a water soluble salt of alkyl sulfates having from about 10 to about 18 carbon atoms in the alkyl radical and water soluble salts of sulfonated monoglycerides of fatty acids having from about 10 to about 18 carbon atoms. For example, the anionic surfactant may be or include, sodium lauryl sulfate, sodium lauroyl sarcosinate, sodium coconut monoglyceride sulfonates, or the like, or combinations thereof.

In at least one embodiment, the personal care composition may include at least one nonionic surfactant. The nonionic surfactant may function as an emulsifier. Illustrative nonionic surfactants may include, but are not limited to, poloxamers or the like. For example, the nonionic surfactants may include polysorbate 20, poloxamer 407, poloxamer 338, poloxamer 124, or the like, or mixtures thereof. The nonionic surfactants may also include, but are not limited to, ethoxylated and hydrogenated ethoxylated castor oils, such as those commonly designated as PEG NN castor oil or PEG NN hydrogenated castor oil, where "NN" designates the number of ethylene oxide units polymerized onto the castor oil to form the nonionic surfactant. For example, the nonionic surfactants may be or include PEG 16, 20, 25, 30, 40, 50, 60, 80, 100, 200, or combinations thereof. In a preferred embodiment, the nonionic surfactant is PEG 40 hydrogenated castor oil, which is commercially available as CREMOPHOR® RH40 from BASF Corp. of Florham Park, N.J.

Unless otherwise specifically identified, the ingredients for use in the compositions and formulations of the compositions disclosed herein are preferably cosmetically or orally acceptable ingredients. As used herein, the expression "cosmetically acceptable" may refer to a component or ingredient that is suitable for use in a formulation for topical application to human skin. A cosmetically acceptable excipient, may refer to an excipient that is suitable for external application in the amounts and concentrations contemplated in the formulations of the compositions disclosed herein, and includes for example, excipients which are "Generally Recognized as Safe" (GRAS) by the United States Food and Drug Administration (FDA). As used herein, "orally acceptable" may refer any ingredient that is present in a composition as described in an amount and form which does not render the composition unsafe for use in the oral cavity.

Methods

The present disclosure may provide methods for preparing a personal care composition having increased foam generation as compared to conventional personal care compositions. The method may include mixing, stirring, combining, or otherwise contacting a carrier and at least two hydrocolloids with one another. In at least one embodiment, the hydrocolloids may include at least xanthan gum and carrageenan. The xanthan gum and the carrageenan may be combined in a synergistic ratio. For example, the xanthan gum and the carrageenan may be combined at a ratio of from about 1.5:1 to about 9:1, more preferably about 2.3:1 to about 9:1, or from about 2.3:1 to about 4:1.

The present disclosure may also provide methods for cleaning skin. The method may include contacting any of the personal care compositions disclosed herein with skin or hair, and optionally, rinsing the personal care composition from the skin or hair with water. In at least one implementation, the personal care composition may be combined or contacted with added water prior to and/or while contacting the personal care composition with the skin or hair. The method may also include dispensing the personal care composition from a container.

The present disclosure may also provide methods for cleaning an oral cavity or a surface thereof. The method may include contacting any of the personal care compositions disclosed herein with the oral cavity or the surface thereof, and optionally, rinsing the personal care composition from the oral cavity or the surface thereof with water. In at least one implementation, the personal care composition may be combined or contacted with added water prior to and/or while contacting the personal care composition with the oral cavity or the surface thereof. The method may also include dispensing the personal care composition from a container.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

Exemplary personal care compositions including varying amounts of one or more hydrocolloids were evaluated for their efficacy in generating foam or foam volume. Particularly, a series of personal care compositions (1)-(5) were prepared by combining the ingredients/components according to Table 1. It should be appreciated that with the exception of xanthan gum and carrageenan, all other components of the personal care compositions (1)-(5), which are denoted as "excipients," including the surfactants, were the same and were maintained at the same concentration or amount. As such, it should be appreciated that any observed or measured properties of the personal care compositions (1)-(5) are attributed to the presence, amount, and/or ratio of xanthan gum and/or carrageenan.

TABLE 1

Composition of Personal Care Compositions (1)-(5)

| Ingredients/Components | 1 | 2 | 3 | 4 | 5 |
| --- | --- | --- | --- | --- | --- |
| Deionized Water (wt %) | QS | QS | QS | QS | QS |
| Xanthan Gum (wt %) | 1.0 | 0.9 | 0.8 | 0.7 | 0.6 |
| Carrageenan (wt %) | 0 | 0.1 | 0.2 | 0.3 | 0.4 |
| Surfactants (wt %) | 25.4 | 25.4 | 25.4 | 25.4 | 25.4 |

TABLE 1-continued

Composition of Personal Care Compositions (1)-(5)

| Ingredients/Components | 1 | 2 | 3 | 4 | 5 |
| --- | --- | --- | --- | --- | --- |
| Excipients (wt %) | 15.5 | 15.5 | 15.5 | 15.5 | 15.5 |
| Total (wt %) | 100 | 100 | 100 | 100 | 100 |

To evaluate the efficacy for producing foam, a Krüss Dynamic Foam Analyzer (DFA100), commercially available from Krüss GmbH of Hamburg, Germany, was utilized. The Krüss Dynamic Foam Analyzer was adjusted according to the parameters/testing conditions indicated in Table 2.

TABLE 2

Parameters of Krüss Dynamic Foam Analyzer

| PARAMETER | TESTING CONDITION |
| --- | --- |
| Sample Concentration | 20% |
| Stirring Speed | 3,000 RPM |
| Oscillation Intervals | 2 sec |
| Foam Time | 30 sec |
| Delay Time | 300 sec |

The results of the foam generation for each of the personal care compositions (1)-(5) are summarized in Table 3 and illustrated in FIG. 1.

TABLE 3

Foam Generation in Personal Care Compositions (1)-(5)

| # | Description of Composition | Maximum Foam Volume (mL) |
| --- | --- | --- |
| (1) | Only Xanthan Gum | 74 |
| (2) | 9:1 Ratio of Xanthan Gum to Carrageenan | 75 |
| (3) | 8:2 (4:1) Ratio of Xanthan Gum to Carrageenan | 81 |
| (4) | 7:3 (2.3:1) Ratio of Xanthan Gum to Carrageenan | 82 |
| (5) | 6:4 (1.5:1) Ratio of Xanthan Gum to Carrageenan | 77 |

As summarized in Table 3 and illustrated in FIG. 1, the combination of xanthan gum and carrageenan in a ratio of from about 6:4 (or 1.5:1) to about 9:1 surprisingly and unexpectedly exhibited synergistic results with respect to the generation of foam. The surprising and unexpected increase in foam generation is especially demonstrated when xanthan gum and carrageenan are provided in a ratio of from about 7:3 (or 2.3:1) to about 9:1. Without being bound by theory, it is believed that the increased foam generation is at least partially attributed to the structure, charge, and/or interactions of the xanthan gum and carrageenan with one another.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A personal care composition, comprising: a carrier and at least two hydrocolloids, wherein the at least two hydrocolloids are present in an effective amount to produce increased foam volume;

wherein the at least two hydrocolloids are present in an amount of greater than 0.1 weight %, based on a total weight of the personal care composition;

wherein a first hydrocolloid of the at least two hydrocolloids comprises a sulfated polysaccharide;

wherein a second hydrocolloid of the at least two hydrocolloids comprises xanthan gum;

wherein the xanthan gum and the sulfated polysaccharide are present in the personal care composition in a ratio of from 2.3:1 to 4:1;

wherein the personal care composition is selected from the group consisting of a shampoo, a shower gel, a body wash, an oral care composition, and a face wash; and wherein the total amount of the hydrocolloids present in the personal care composition is from 0.5 weight % to 1.5 weight %, based on a total weight of the personal care composition.

2. The personal care composition of claim 1, wherein the sulfated polysaccharide comprises one or more of carrageenan, keratan sulfate, chondroitin sulfate, dextran sulfate, dermatan sulfate, fucoidan, funoran, heparin, porphyran, or combinations thereof.

3. The personal care composition of claim 1, the sulfated polysaccharide is selected from the group consisting of carrageenan, keratan sulfate, chondroitin sulfate, dextran sulfate, dermatan sulfate, fucoidan, funoran, heparin, porphyran, and combinations thereof.

4. The personal care composition of claim 1, wherein the sulfated polysaccharide is carrageenan present in 0.7-0.8 weight %, based on a total weight of the personal care composition.

5. The personal care composition of claim 4, wherein the carrageenan comprises one or more of kappa-carrageenan, iota-carrageenan, lambda-carrageenan, or a combination thereof.

6. The personal care composition of claim 4, wherein the xanthan gum and the carrageenan are present in the personal care composition in a ratio of about 2.3:1.

7. The personal care composition of claim 4, wherein the xanthan gum and the carrageenan are present in a total amount of about 1.0 weight %, based on a total weight of the personal care composition; and wherein the xanthan gum and the carrageenan are present in a ratio of about 2.3:1.

8. The personal care composition of claim 1, wherein the xanthan gum and the sulfated polysaccharide are present in the personal care composition in a ratio of about 2.3:1.

9. The personal care composition of claim 1, which is an oral care composition, wherein the carrier is an orally acceptable vehicle, and wherein the oral care composition is selected from the group consisting of a toothpaste and a tooth gel.

10. A method for preparing the personal care composition of claim 1, the method comprising contacting the carrier and the at least two hydrocolloids with one another.

11. A method for generating increased foam volume in a personal care composition selected from the group consisting of a shampoo, a shower gel, a body wash, an oral care composition, and a face wash, the method comprising contacting a carrier of the personal care composition with at least two hydrocolloids, wherein the at least two hydrocolloids comprise xanthan gum and carrageenan in a ratio of from 2.3:1 to 4:1; and wherein the xanthan gum and carrageenan are present in an amount of from 0.5 weight % to 1.5 weight %, based on a total weight of the personal care composition.

* * * * *